United States Patent
Hancu et al.

(10) Patent No.: US 9,974,521 B2
(45) Date of Patent: May 22, 2018

(54) COMPUTER-AIDED LESION DETECTION AND TRACK PLANNING FOR MRI-GUIDED BREAST BIOPSY

(71) Applicant: GENERAL ELECTRIC COMPANY, Schenectady, NY (US)

(72) Inventors: Ileana Hancu, Clifton Park, NY (US); Robert David Darrow, Scotia, NY (US); Eric William Fiveland, Niskayuna, NY (US); Xiaofeng Liu, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days. days.

(21) Appl. No.: 14/618,316

(22) Filed: Feb. 10, 2015

(65) Prior Publication Data

US 2016/0228104 A1 Aug. 11, 2016

(51) Int. Cl.
*A61B 5/00* (2006.01)
*A61B 10/02* (2006.01)
*A61B 5/055* (2006.01)

(52) U.S. Cl.
CPC ........ *A61B 10/0233* (2013.01); *A61B 5/0555* (2013.01); *A61B 5/4312* (2013.01); *A61B 5/742* (2013.01); *A61B 2576/02* (2013.01)

(58) Field of Classification Search
CPC ................ A61B 5/4312; G06T 7/0081; G06T 2207/30068
See application file for complete search history.

(56) References Cited

U.S. PATENT DOCUMENTS

| | | | |
|---|---|---|---|
| 6,675,037 | B1 | 1/2004 | Tsekos |
| 7,556,602 | B2 | 7/2009 | Wang et al. |
| 8,412,544 | B2 | 4/2013 | Reiner |
| 8,423,120 | B2 | 4/2013 | Tynes et al. |
| 8,792,965 | B2 | 7/2014 | Ning et al. |
| 2006/0171573 | A1* | 8/2006 | Rogers ............ G06K 9/3233 382/128 |
| 2009/0135191 | A1* | 5/2009 | Azar ............ A61B 6/502 345/522 |
| 2013/0185096 | A1 | 7/2013 | Giusti et al. |

OTHER PUBLICATIONS

Liberman et al, Fast MRI-Guided Vacuum-Assisted Breast Biopsy, AJR:181, Nov. 2003.*
Ralleigh et al., "Image guided breast biopsy", International journal of clinical practice, vol. 56, issue 8, pp. 583-587, 2002.

(Continued)

*Primary Examiner* — Serkan Akar
(74) *Attorney, Agent, or Firm* — Pabitra K. Chakrabarti

(57) ABSTRACT

The system and method of the invention pertains to an MR-guided breast biopsy procedure, specifically as to quickly identifying the biopsy location. More particularly, the system utilizes a diagnostic imaging modality such as magnetic resonance imaging (MRI) to locate one or more lesions in a human breast. Non-rigid registration between uncompressed screening images (where the lesion has been previously identified) and the compressed biopsy images enables easier identification of the biopsy site, hence shortening the biopsy procedure.

6 Claims, 10 Drawing Sheets

(56) References Cited

OTHER PUBLICATIONS

"Image-Guided Vacuum-Assisted Breast Biopsy for Suspicious, Non-Palpable Breast Lesions", AHFMR (Alberta Heritage Foundation For Medical Research), pp. 1-42, Aug. 2005.
"Breast Imaging and Intervention", Canada Association of radiologists , pp. 1-45, Sep. 29, 2012.
Smetherman, "Screening, Imaging, and Image-Guided Biopsy Techniques for Breast Cancer", Surgical Clinics of North America, vol. 93, Issue 2, Apr. 2013, pp. 309-327, Apr. 2013.

* cited by examiner

Patient A          Patient B

COMPUTER-AIDED LESION DETECTION AND TRACK PLANNING FOR MRI-GUIDED BREAST BIOPSY

STATEMENT AS TO FEDERALLY SPONSORED RESEARCH & DEVELOPMENT

This invention was made with Government support under contract number R01CA154433 awarded by the National Institutes of Health through the National Cancer Institute. The Government has certain rights in the invention.

FIELD

Embodiments relate generally to the field of imaging and biopsy, and more particularly to computer-aided lesion detection, track planning and quality assurance for Magnetic Resonance Imaging (MRI) guided breast biopsy.

BACKGROUND

Breast cancer is the second leading cause of death in women. While death rates have been declining in the last 20 years, these decreases are believed to be the result of increased awareness, improved treatment, and earlier detection through screening. While X-ray mammography is the first line of attack for breast cancer screening, it has its limitations, especially for high-risk women. Thus, high-risk women are generally screened using MRI. Given the success of MRI in the past few years, clinical trials are now evaluating the extension of MRI-based breast cancer screening programs to medium-risk women. In recent reports, evidence shows that breast cancers can be detected even with abbreviated (i.e. 3 minute) MRI exams. While MRI sensitivity in detecting breast lesions is very high, its specificity is lower. Specifically, between about 55%-70% of suspicious MRI lesions are benign on pathology reports. Consequently, women need to undergo biopsies to confirm or refute the positive screening results. Typically, a targeted ultrasound is done following the detection of an MRI positive lesion to determine if the lesion can be biopsied under ultrasound guidance. Unfortunately, a sonographic correlation can only be found for 23-89% of such lesions. Therefore, a good fraction of biopsy procedures need to be guided by MRI, or not be performed at all. Although MRI-guided breast biopsy systems are widely available, many radiologists prefer to biopsy with ultrasound, as this is perceived to be more easily performed. In addition, while 55% of the sites owning a whole-body scanner worldwide perform breast MRI, only 5% of these sites perform interventional procedures.

There are a number of reasons why MRI-guided biopsies are not more common. To better understand their shortcomings, the tools of the procedure are highlighted in FIG. 1, and described as follows. The biopsy setup 100 is depicted in FIG. 1 as an assembled biopsy setup (a) and as separate components (b).

While a woman patient is positioned supine on a breast coil, the breast to be biopsied is compressed between a coarse plastic grid 101 and an immobilization, or compression plate (e.g. behind the grid in the lower-most image of FIG. 1). The grid typically has openings 103 sized 2 cm×2 cm. Each of the grid openings accepts a sub-grid insert 105 which contains a matrix of 3×3 insertion locations 107. The woman is advanced in the MRI scanner, and a contrast agent is administered to localize the lesion. A fiducial marker on the coarse grid 101 is used to identify lesion position relative to the biopsy device. The biopsy location is then defined by the clinician. This may be a time-consuming step, as the screening and biopsy images may be acquired in different orientations. Moreover, the screening images are acquired with the breasts uncompressed, while the biopsy images are acquired with the breast compressed. The compression can limit perfusion, hence causing the suspicious lesion not to enhance anymore. Following lesion identification, software computes the entry position (i.e., coarse grid position and grid insert position) and lesion depth, and reports it on the computer screen in the scanner control room. Typically, given the single degree of freedom available for biopsy tool advancement, a single entry location is possible for a given lesion. At this point, the patient is removed from the magnet, while the compressed breast containing the lesion remains in a fixed position. The clinician enters the scanner room, identifies the entry location (i.e., coarse grid row and column, as well as grid insert row and column) and inserts a stylet 109 into an introducer 111, then into the grid insert 105, and then into the coarse grid 101. Once a particular grid entry point is chosen, a single degree of freedom is allowed for the biopsy device, which can only advance orthogonal, at right angles, to the grid plane. The introducer has depth markings, and a moveable, friction-fit ring 112 to control the depth of its insertion into the breast. The stylet is advanced to the approximately depth into the breast (defined manually by the setting of the friction-fit ring by the physician), then replaced with a plastic obturator 113. The medical team leaves the room and the patient is re-imaged to confirm if the tip of the obturator is at the location of the lesion. Assuming image confirmation, the patient is taken out of the magnet again, the obturator is replaced with the biopsy gun, and biopsy samples are taken (e.g., by rotating the biopsy gun multiple times). At the end of the procedure, the biopsy gun is replaced with the obturator, the patient is advanced to the scan position, and another image is acquired, for visual assessment of biopsy success.

Prior art techniques, such as that described above, make MRI-guided breast biopsy workflow cumbersome, resulting in a procedure completion time of 30-60 min. This utilizes a large fraction of MRI scanner time, numerous personnel (e.g., interventional radiologist, nurse and scanning technologist), and drives cost high. The MRI-guided biopsies are conducted without real-time guidance. Thus, lesions can only be visualized for ~10 minutes after the contrast agent was injected, while the woman is inside the MRI magnet. The biopsies are performed, however, outside the MRI magnet, with the women on the MRI table. Accuracy is limited given the 6 mm (or 8 mm) distance between possible adjacent insertion points (and depending on whether the adjacent insertion points fall within the same opening of the coarse grid or not). See FIG. 1. Thus, this also limits the locations where the tip of the biopsy needle can reach. Larger than needed tissue volume is therefore extracted to sample at least a fraction of the enhanced lesion.

In comparison, core biopsies, as typically performed for breast lesions under ultrasound guidance, employ 11-18 gauge needles (with 14 gauge being typical) and extract about 4 samples/lesion (for about 80 mg total mass of extracted tissue); vacuum assisted biopsies for MRI-guided biopsies typically employ 9 gauge needles and extract about 8 samples/lesion (for a total mass of extracted tissue of about 1.5 g). The lack of real-time guidance, the limited number of entry points, and the orthogonal advancement requirement make it difficult for the clinician to access lesions requiring high accuracy, such as the ones close to silicone implants. In addition, lesions located outside of the compression grid (e.g., posterior) are very difficult to access with any kind of accuracy. Furthermore, large blood vessels cannot be avoided; thus, accidental puncture can lead to the creation of a hematoma(s) and morbidity to the patient. In fact, about 1.5% of MRI-guided biopsies are interrupted due to excessive bleeding. Assessment of the biopsy procedure is done at the end visually, with no quantitative tool available to confirm the fraction of the lesion removed. Furthermore, by the end of the procedure, the contrast agent may have already washed out, providing different contrast and slightly different geometry that renders this visual assessment inaccurate.

Given the shortcomings described above, cancers can be missed. In one study, follow-up MRI, after benign and imaging-histology concordant MRI-guided biopsies, has shown that 8-12% of targeted lesions were inadequately sampled; malignancy was ultimately diagnosed in 14-18% of these cases. Follow-up after benign and imaging-histology discordant biopsies indicated malignancies in 13-44% of the lesions initially diagnosed as benign. False negative rates as high as 11.7% were recently reported for MRI-guided biopsies.

To fulfill the true potential of breast MRI as the test with unparalleled sensitivity for breast cancer detection, a simple and accurate solution for MRI guided breast biopsies needs to be devised. Widespread acceptance and practice of these biopsies, as currently implemented, is not practical or economically feasible due to the time, expense and high level of skill associated with current workflow. Further, given the percentage of false negatives, inaccuracy is a significant concern. The lack of a simple solution for MRI-guided breast biopsies will ultimately stunt the growth of breast MRI as a screening modality, and will prevent many women from benefiting from this very sensitive test. A need exists to fundamentally simplify and increase the accuracy of MRI-guided breast biopsy procedures. The invention will address some shortcomings of present day MR-guided biopsy procedures, rendering the procedures shorter in duration, more accurate, and cheaper.

SUMMARY

The system and method of the invention pertains to an MR-guided breast biopsy procedure, specifically as to quickly identifying the biopsy location, planning the biopsy tool path and quantitatively assessing the success of the biopsy procedure. More particularly, the system utilizes a diagnostic imaging modality such as magnetic resonance imaging (MRI) unit to locate and biopsy one or more lesions in a human breast.

In one embodiment, non-rigid registration between uncompressed screening images (where the lesion has been previously identified) and the compressed biopsy images enables easier identification of the biopsy site, hence shortening the biopsy procedure. In addition, for exemplary purposes and not limitation, by segmenting out the blood vessels from the biopsy images, and in combination with a tailored instrument guide insert, the clinician can plan for an instrument track that links the entry point with the lesion, without piercing the blood vessels. This prevents hematoma formation, and thus patient morbidity.

In one embodiment, a method for identifying a lesion within a breast during an interventional MRI-guided breast biopsy procedure is disclosed, the method comprising the steps of: acquiring one or more screening images in a screening exam; segmenting the lesion to create a three dimensional (3D) lesion mask of the segmented lesion on the screening images; acquiring one or more images in an interventional exam to produce interventional images, absent contrast enhancement; providing a computer processor for performing a non-rigid registration procedure between the screening images and the interventional images, such that a transformation is produced to relate the one or more screening images to the one or more interventional images; and displaying the 3D lesion mask on the interventional images to identify a target location of the lesion. In one aspect, the step of displaying the 3D lesion mask on the interventional images occurs during the interventional exam.

In one aspect, during the step of segmenting the lesion, manual seed placement is designated by a clinician. In another aspect, the method further comprises a step of the clinician setting thresholds to grow a 3D volume around the lesion, or use of a computer and algorithm to control a 3D volume expansion.

Embodiments of the invention further utilize a step of performing non-rigid registration comprising (a) starting with a translation of the interventional images in order to overlap a field of view of the interventional images with a field of view of the screening images; and (b) ending with the non-rigid registration procedure based on mutual information shared between the screening images and the interventional images.

Another embodiment describes a method for determining an entry path into a breast during an interventional MRI-guided breast biopsy procedure, the method comprising the steps of: acquiring one or more interventional images in a biopsy exam; identifying a location of a lesion in the breast to be biopsied; segmenting one or more blood vessels using an algorithm run by a computer processor; and predicting an entry point through a biopsy grid that avoids intersecting the one or more blood vessels. In one aspect, a step of identifying includes using computer-aided detection of the lesion by non-rigid registration between one or more screening images and the one or more interventional images. A three-dimensional (3D) mask on the interventional images may also be used to identify a target location of the lesion prior to the step of predicting an entry point. Further, the one or more interventional images may be acquired utilizing a contrast agent.

Embodiments of the invention include a step of advancing a biopsy device through the biopsy grid to a target location of the lesion, such that the step of advancing the biopsy device proceeds without piercing any of the one or more blood vessels. Detailed descriptions of various embodiments are described as follows.

DETAILED DESCRIPTION

Figure 1:
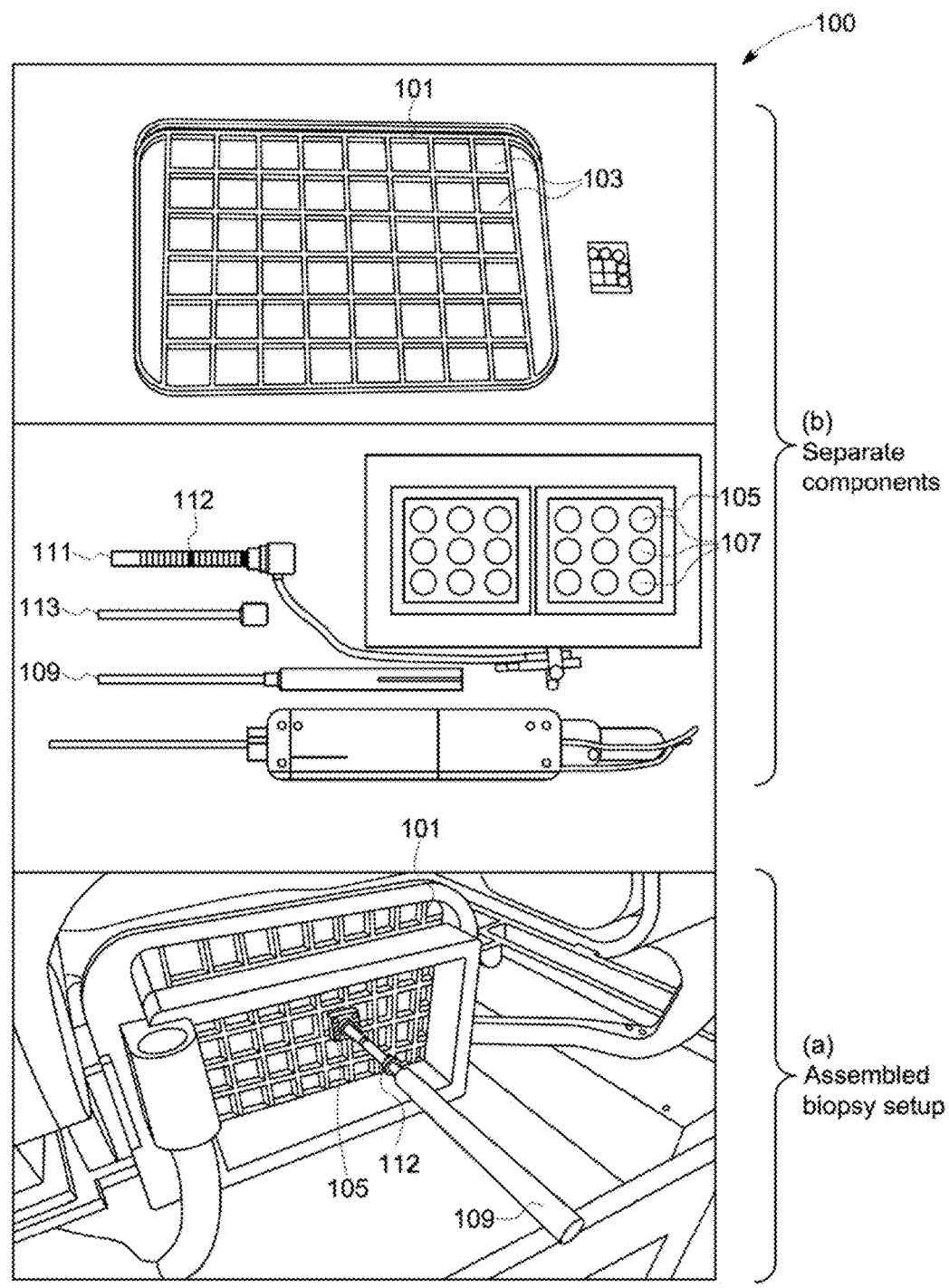
FIG. 1 (PRIOR ART) is an illustration of the tools as currently utilized in biopsy: (a) the assembled biopsy setup; and (b) the separate components as utilized for biopsy procedures.

Various embodiments will be better understood when read in conjunction with the appended drawings. It should be understood that the various embodiments are not limited to the arrangements and instrumentality shown in the drawings.

This invention provides improvement of the MR-guided breast biopsy procedure such that the prior 30-60 min procedure is reduced to duration of about 15 minutes and with greater accuracy. The prior workflow 222 will be described in the following FIG. 2A in greater detail via steps (1a)-(7a). Here, workflow 200 in one embodiment illustrates the simplified procedure for biopsy through computer-aided definition (210) of biopsy entry location using the screening exam and the first biopsy series; defining an entry point for the biopsy device at 220; and advancing the biopsy device to take a biopsy when the tip of the biopsy device reaches the target at 230. This reduces procedure time by half, saving time and expense while also facilitating more efficient patient care.

Figure 2A:
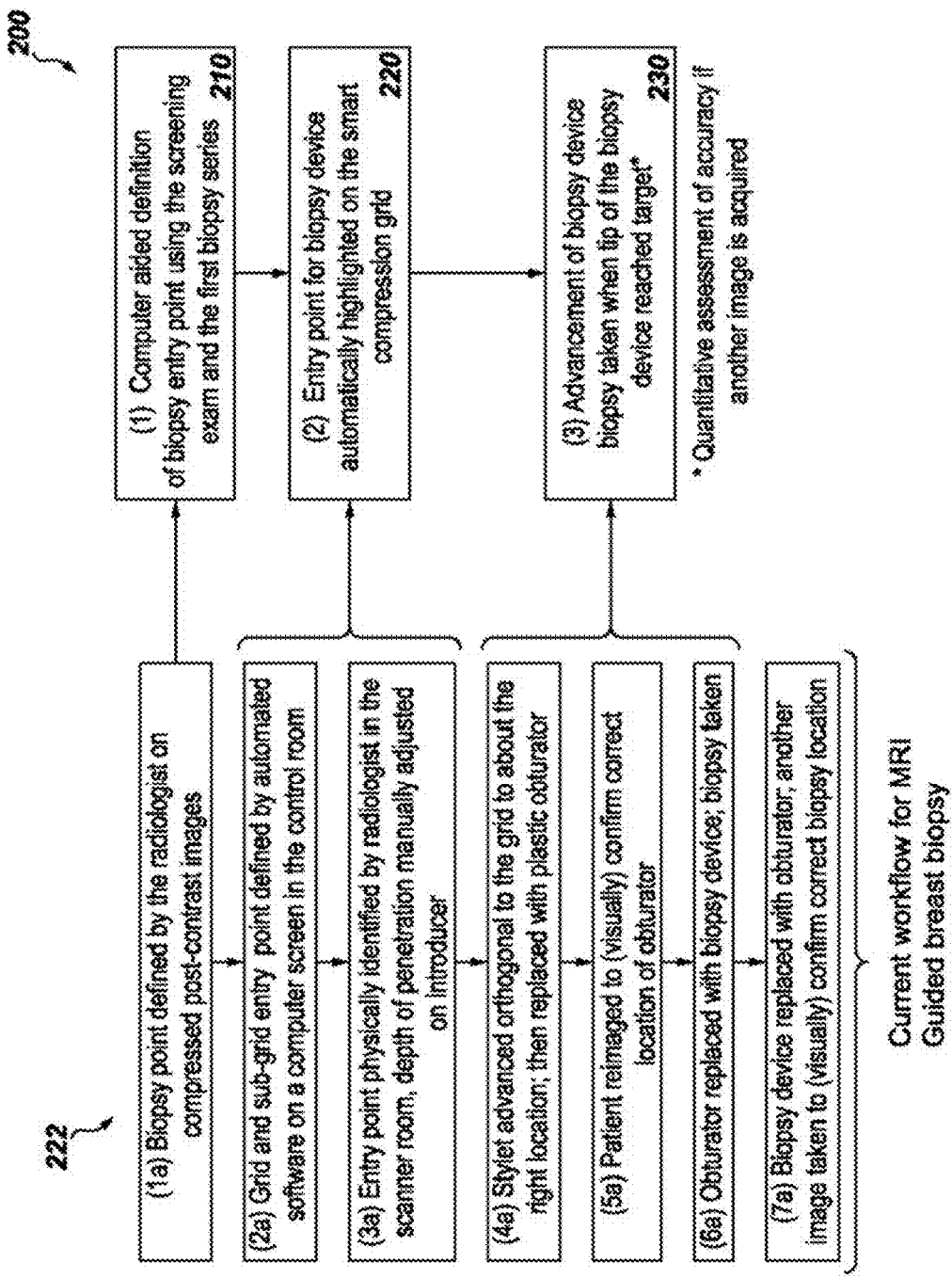
FIG. 2A depicts a schematic for current workflow for MRI-guided breast biopsy (PRIOR ART).

In the systems of 30-60 minute duration as shown in FIG. 2A, multiple steps comprise the following: (1a) The radiologist identifies the biopsy location on the interventional images (e.g. often on compressed post-contrast images); (2a) the grid and sub-grid entry point are defined by automated software on a computer screen in the control room; (3a) the entry point is then physically identified by the radiologist in the scanner room, with the depth of penetration manually adjusted on the introducer; (4a) the stylet is then advanced orthogonally to the grid to about the desired location, then replaced with the plastic obturator; (5a) the patient is re-imaged to visually confirm appropriate location of the obturator; (6a) the obturator is replaced with biopsy device and biopsy taken; and (7a) the biopsy device is replaced with the obturator, followed by another image being taken to visually confirm the appropriate biopsy location.

Figure 2B:
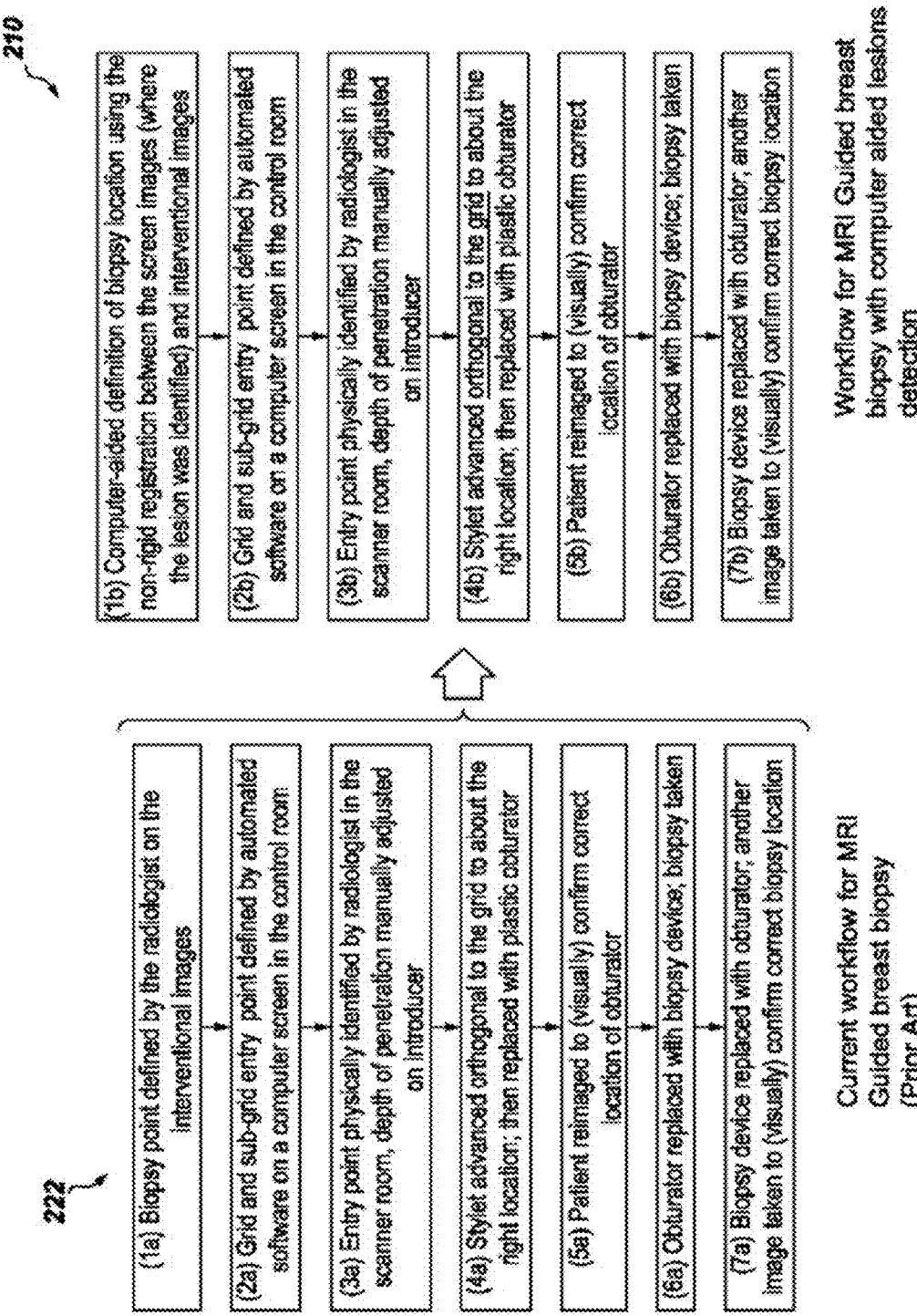
FIG. 2B depicts a schematic illustrating workflow for MRI-guided breast biopsy with computer-aided lesion detection in one embodiment of the invention.

In contrast, the MR-guided biopsy workflow of one embodiment of the invention in FIG. 2B takes about 15 minutes and utilizes computer-aided detection (210) in breast biopsy to include the steps of: (1b) computer-aided definition of the biopsy entry location using non-rigid registration between the screening exam images (where the lesion was identified) and the interventional images; (2b) designating entry point for the biopsy device as automatically highlighted on the compression grid (e.g. the grid and sub-grid entry point is defined by automated software on a computer screen in the control room); (3b) the entry point is physically identified by a radiologist in the MR scanner room, the depth of penetration manually adjusted on the introducer; (4b) the stylet is advanced orthogonal to the grid adjacent the designated location, where plastic obturator is replaced; (5b) the patient is re-imaged to visually confirm designated location of the obturator; (6b) the obturator replaced with a biopsy device and the biopsy taken; and then, (7b) the biopsy device is replaced with the obturator, another image taken to visually confirm the designated biopsy location. The biopsy is taken when the tip of the biopsy device reaches the target. Accuracy is quantitatively assessed if and when another image is acquired. Detailed description of computer-aided lesion detection 210 (See also FIG. 2B, Step (1b)) is also depicted in an embodiment 300 of FIG. 3.

Figure 3:
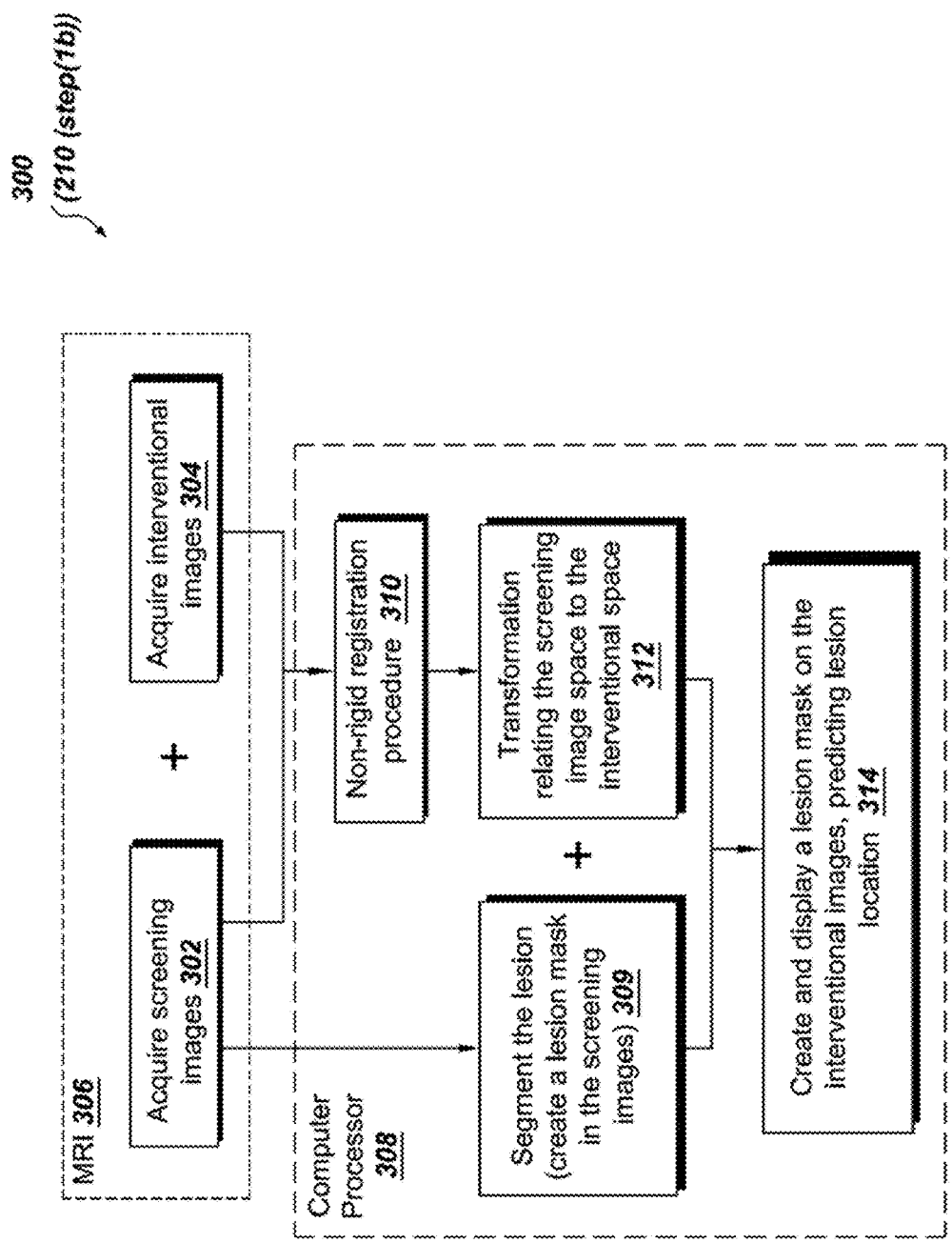
FIG. 3 illustrates a flow diagram as to an embodiment of the invention to identify a lesion in a breast by way of computer-aided lesion identification in a biopsy exam.

The schematic of FIG. 3 sets forth methodology for computer-aided lesion identification 300 in a biopsy exam. Initially, screening images 302, as well as interventional images 304, are acquired by MRI unit 306. A computer processor 308 segments the lesion at 309 to create a lesion mask on the screening images. Non-rigid registration 310 creates a transformation 312 relating the screening image space to the interventional image space. By applying this transformation to the lesion mask segmented from the screening images, a new lesion mask is depicted on the interventional images 314 to display the location of the target lesion. In one aspect, the computer processor may also utilize manual input. For exemplary purposes, and not limitation, the clinician may click once on a lesion to start the mask creation process; the computer then grows the lesion to a 3D volume.

Embodiments of the invention can be modified and implemented to improve MR-guided breast biopsy procedure as herein described. Specifically, as disclosed here, the method includes the steps as follows:

(a) Using non-rigid registration between the uncompressed screening images (with the lesion already identified) and the compressed biopsy images, a breast area is suggested to a clinician as the most likely location of the tumor in the biopsy exam. This enables easier identification of the biopsy site, hence shortening the biopsy procedure. It also enables identification of the lesion in cases in which perfusion is reduced due to compression, the compression of which causes the lesion not to enhance any more.

(b) Based on the large vessels segmented out of the first post-contrast biopsy series, a track is suggested that comprises the lesion and the tip of the biopsy stylet, and further avoids the large vessels. This avoids hematoma formation, and hence prevents patient morbidity. See FIG. 2C.

(c) Following automated lesion segmentation in the first post-contrast biopsy image, and the biopsy location segmented out of last biopsy series, a quantitative assessment is offered at the end of the procedure, highlighting the volume of tissue taken out, and the % lesion fraction of the extracted tissue. This offers confirmation to the clinician that the correctly identified tissue, as desired, was sampled during the procedure.

Figure 2C:
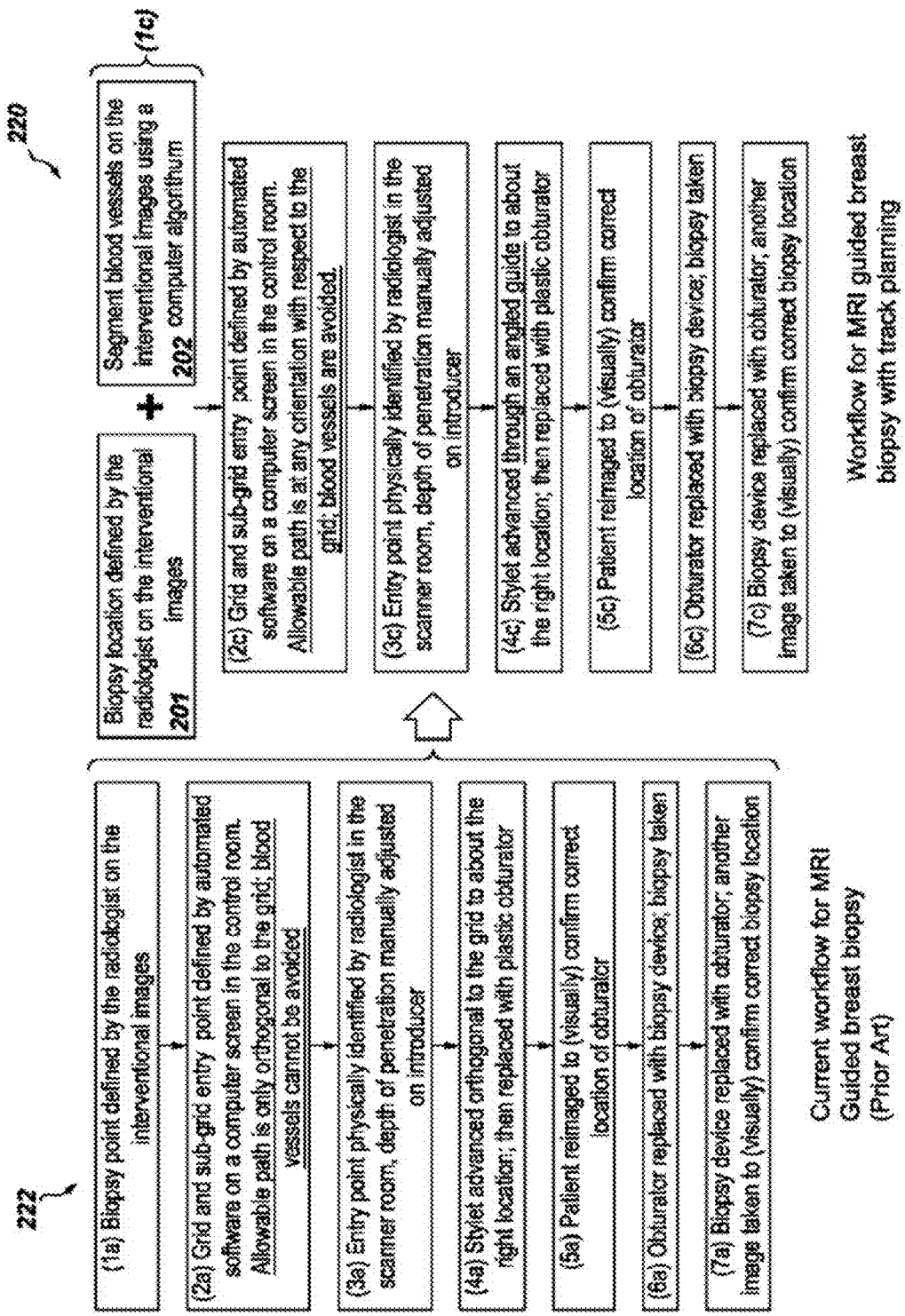
FIG. 2C illustrates a schematic of workflow for MRI-guided breast biopsy with track planning in another embodiment.

Another embodiment of the invention in FIG. 2C is compared with the current workflow for MRI-guided breast biopsy of FIG. 2A. Specifically, the workflow for MRI-guided breast biopsy with track planning 220 in the invention is initiated at step (1c) where the biopsy location is defined (201) by the radiologist on the interventional images and blood vessels are segmented (202) on the interventional images using a computer algorithm. At step (2c), the grid entry point and sub-grid entry point, in combination are defined by automated software on a computer screen in the control room. The allowable path is at any orientation with respect to the grid so that blood vessels are avoided. In contrast, current rudimentary workflow for MRI guided breast biopsy at step (2a) in the schematic has an allowable path restricted orthogonal to the grid such that blood vessels cannot be avoided.

Continuing with track planning of FIG. 2C at step (3c), the entry point is physically identified by a radiologist in the scanner room, the depth of penetration manually adjusted on the introducer. At step (4c), the stylet is advanced through an angled guide to about the designated position and then replaced with the plastic obturator. The patient is re-imaged (5c) to visually confirm the location of the obturator. The obturator is replaced (6c) with the biopsy device and the biopsy taken. At conclusion, the biopsy device is replaced with the obturator (7c), another image taken to visually confirm appropriate designated biopsy location.

Figure 2D:
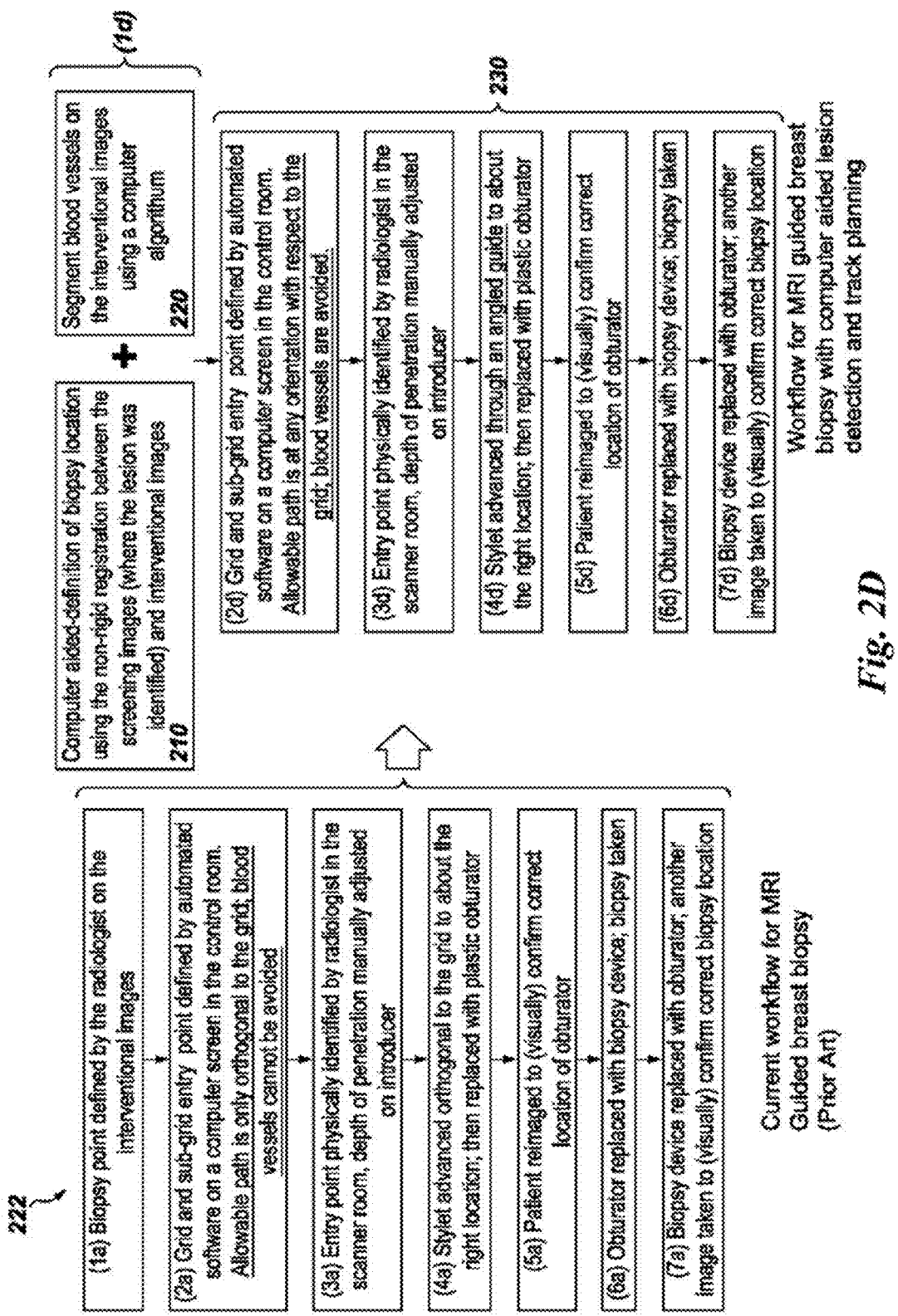
FIG. 2D illustrates a schematic of workflow for MRI-guided breast biopsy with computer-aided lesion detection in combination with track planning.

Embodiments of the invention may utilize MRI-guided breast biopsy alone with computer aided lesion detection or track planning, or the techniques may be utilized in combination. As shown in FIG. 2D, computer-aided lesion detection 210 is utilized in combination with track planning 220 to designate at least one allowable path (2d) at various orientations through the grid to the lesion in a breast. One or more paths may be designated and selected as based upon the least intrusive and less obstructive path to the lesion, the paths presented [via computerized display] at a variety of orientations through the compression grid and grid insert. The advancement of the biopsy device to the lesion and tissue extraction by biopsy (230) is then concluded via steps (2d)-(7d) as described similarly in FIGS. 2B and 2C of steps (2b)-(7b) and steps (2c)-(7c), respectively.

Figure 7:
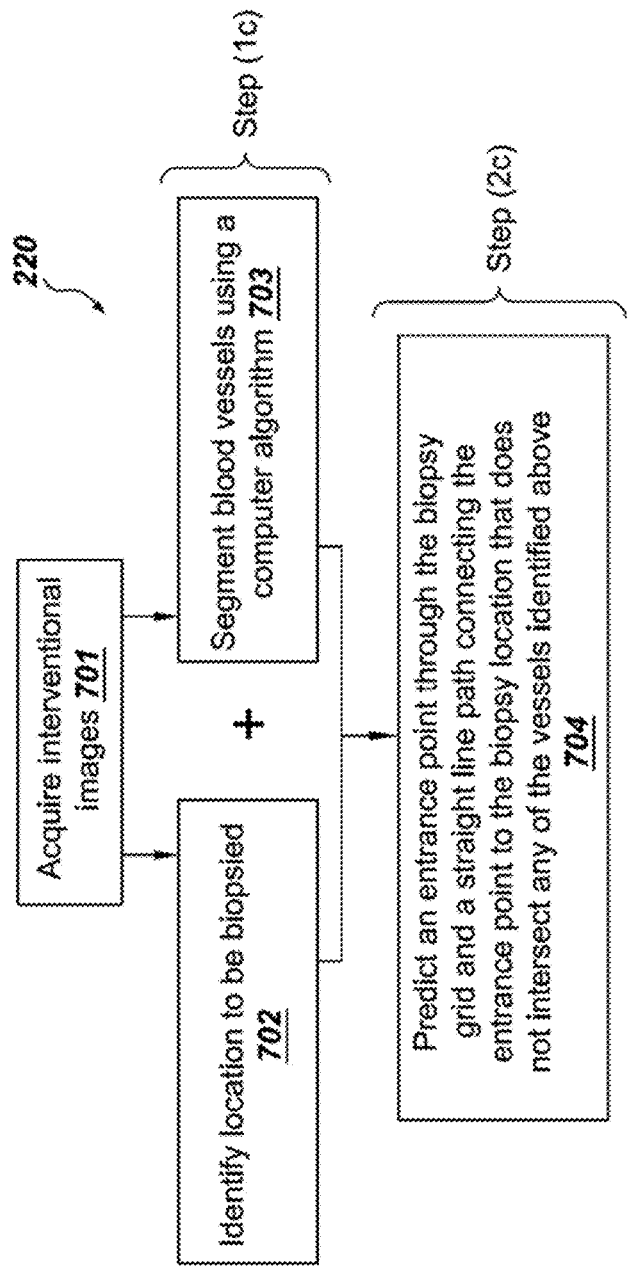
FIG. 7 depicts a schematic of the invention which utilizes track planning to predict an entry point through a biopsy grid without piercing blood vessels.

A more detailed schematic of one embodiment of the invention is depicted in FIG. 7. The step of track planning 220 illustrates the acquisition 701 of interventional images, identification 702 of the lesion to be biopsied, in combination with segmenting 703 blood vessels using a computer algorithm. An entrance point through the biopsy grid is then predicted 704 such that a straight line path connecting the entrance point to the biopsy location is identified that does not intersect any of the vessels segmented above.

Lesion identification 702 can be done manually by the clinician while using the interventional images. The output of the identification process is usually a single point in 3D space, but may also be a volume. In another aspect, lesion identification 702 can also be performed by the computer, using just the interventional images. This assumes that contrast is given in the interventional images, and that the lesion enhances in the interventional exam. In yet another aspect, lesion identification 702 can be performed by using the computer, using the screening images with the lesion identified, and the interventional images.

Further, aspects of the invention confirm immobilization of a human or animal breast during biopsy; perform non-rigid registration between the axial screening images (with the lesion already identified) and the compressed sagittal biopsy images; and develop a quality control tool to confirm and validate success of the procedure, such success measured by the accuracy of biopsy, including determining volume of tissue removed and the percentage of lesion fraction in the extracted tissue.

Confirmation of Breast Immobility During Biopsy

Figure 4:
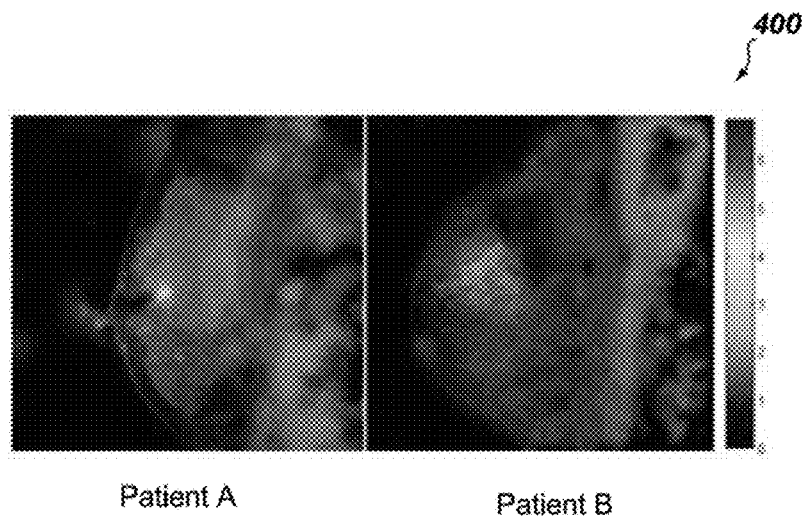
FIG. 4 illustrates tissue displacements (e.g. millimeter dimensions) recorded between the start and end of biopsy exams in Patient A and Patient B.

To validate breast immobility during the biopsy procedure, four pre- and post-biopsy patient data sets were analyzed. The results from two of these patients are presented in FIG. 4. After performing non-rigid, registration 400 between the first (contrast) series and the last series in a biopsy exam (i.e., confirming biopsy location), pixel displacement was measured as a function of position. FIG. 4 displays the displacements recorded in a slice from two patients, Patient A and Patient B. The average displacement over the breasts of four separate patients during the biopsy procedure was about 0.8 mm with higher displacements around the biopsy site, up to about 3.5 mm displacements. In another example, the 9-gauge biopsy tools have about 4 mm diameters, and larger displacements around the biopsy site are therefore expected. Aspects of the invention are demonstrated by the images of FIG. 4 which show that the breast does not move during the biopsy procedure. For example, if a lesion is identified at the beginning of the procedure, the lesion stays put and does not move during the biopsy process. In other words, if the first series in the biopsy exam (the series without contrast) is registered with the screening exam, then this is as useful as registering a later (e.g. a $5^{th}$ series, etc.) series from the biopsy exam (that may utilize contrast) with the screening exam. The $5^{th}$ series is utilized here for exemplary purposes, and any series may be utilized in comparison, including but not limited to a $3^{rd}$, $4^{th}$, etc.

Computer-Aided Lesion Identification

By way of computer-aided lesion identification, lesions in biopsy exams are located based on their locations in the screening scans. Embodiments of the invention automatically register the [uncompressed] screening series to the [compressed] biopsy series. Following registration, the three-dimensional (3D) lesions segmented from the screening series is transformed in the biopsy frame of reference. This allows the clinicians to quickly locate the lesion, thus shortening the biopsy planning time. Automatic registration for this task is difficult, as the two series can have different orientations, spatial resolutions and spatial coverage. Moreover, the often large breast deformation caused by compression cannot be handled well by most existing registration methods. To address these issues, a fast learning-based method first determines the field of view (FOV) overlap regions of the two scans. In one aspect, a fast non-rigid registration method can account for the large breast deformation by leveraging existing techniques. In another aspect, a finite-element based method can be incorporated to correctly model the breast tissue properties and increase registration accuracy. As a result, it is a goal to highlight to the clinician a region no larger than about 5 mm past the edges of the lesion as the likely lesion location. Using this aid, the clinician has discretion to decide on the specific biopsy site.

In another embodiment, registration between the screening (contrast enhanced) series and the first non-contrast biopsy series; and between the screening series to the first contrast series from the biopsy exam is performed. The lesion location suggested by the first registration process is then compared to the lesion location suggested by the second registration, and with the lesion finally selected to biopsy. Whether the three locations largely coincide questions the use of contrast administration during biopsy. In other words, lesion detection and biopsy may be performed without contrast. See FIG. 3.

Preliminary Non-Rigid Registration Between Uncompressed Axial Screening Images and Compressed Sagittal Biopsy Images Lesion identification in the biopsy exam is not always straightforward. The screening exam and the biopsy exams are often acquired in different orientations (e.g. axial vs. sagittal). The image resolution of biopsy images can be lower than the image resolution in the screening images, thus making small lesions hard to find. Breast compression distorts the anatomy and can cause large deformations. Moreover, compression can limit perfusion, causing the lesions limiting enhancement of the lesion in the biopsy series. These issues make it difficult to relocate the lesions in the biopsy scan; sometimes numerous post-contrast scans, image reformatting, image subtraction and maximum intensity projection (MIP) map generation are needed, hence lengthening the biopsy procedure.

In order to shorten and simplify lesion identification in the biopsy exam, embodiments of the invention register two sets of images. The compressed sagittal image (acquired in the biopsy series) is first translated to overlap the field of view of the (axial) screening series. Non-rigid registration between the two data sets is then employed to account for the deformation caused by the compression. Aspects of the invention may be modified as thus described to integrate multiple sets of images, as desired and appropriate given the goal to minimize procedure timeframe.

Figure 5:
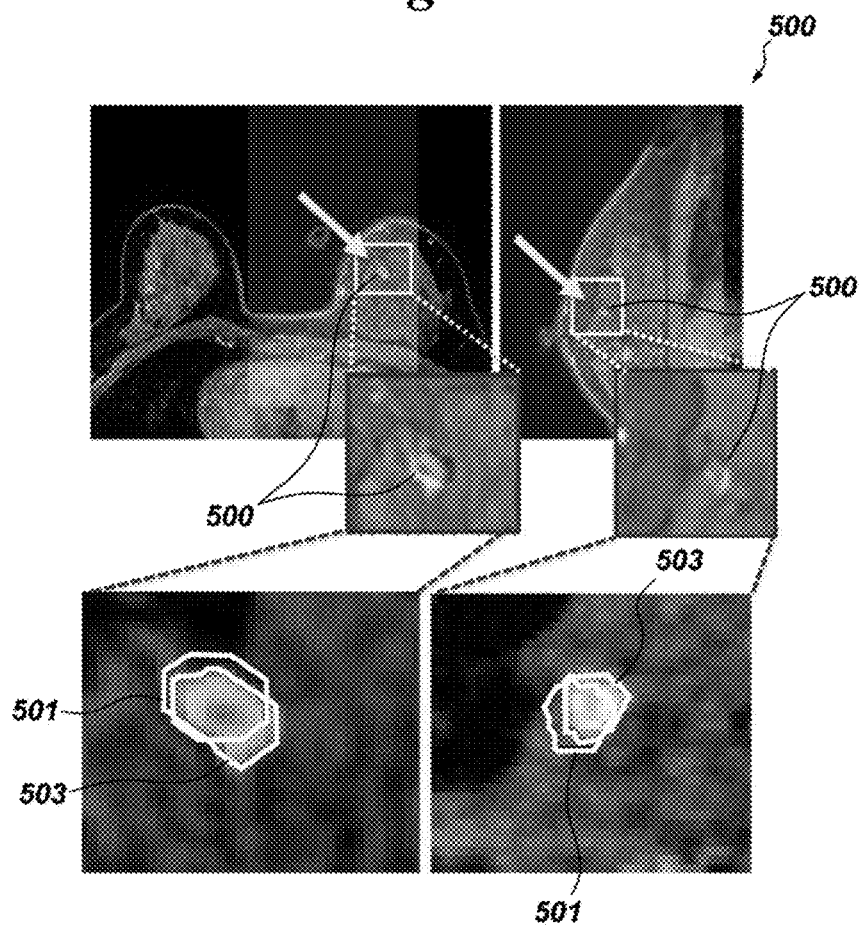
FIG. 5 depicts an embodiment of the invention including an axial view of the breast and a sagittal view, and depicting overlay between the predicted lesion location obtained through the workflow of FIG. 3, and the actual lesion in which the lesion is enhanced in the interventional images. Magnified regions of the lesion are displayed in the lower row of images.

FIG. 5 depicts lesion region 500 segmented during the contrast enhanced registration process. FIG. 5(a) is an axial view of the breast; FIG. 5(b) is a sagittal view. After applying the non-rigid registration, the computer processor automatically segments lesions from the screening exam and biopsy exam (with contrast enhancement utilized here). The biopsy image 501 of the lesion is outlined by 501 and the predicted lesion location 503 is outlined by 503 for clarity of depiction in the current images. As utilized to evaluate the performance of both the reproducibility of manual segmentations and the spatial overlap accuracy of automated probabilistic fractional segmentation of MR images, the Dice similarity coefficient (DSC) between the two lesion regions was 0.66, and the distance between the center of the lesions in the screening images and the biopsy images after registration was 1.42 mm. In one aspect, then, a slight error in volume re-localization is due to the different resolutions of the screening and the biopsy regions. Further, the overlay depicted in FIG. 5 explains the predicted location of the tumor in context with actual tumor location.

Biopsy Track Planning

One embodiment of the invention identifies the large vessels in the breast tissue and plans for a biopsy track that avoids the vessels, and therefore prevents formation of large hematomas during the biopsy procedure. Some work to segment large vessels in breast MRI exams was previously performed as a means to reduce classifying vascular pixels as suspicious on Dynamic Contrast Enhanced-MRI computer-aided diagnostic (CAD) platforms, or for enhanced treatment monitoring through vasculature parameter mapping. While gradient-based algorithms for the analysis of typical MR angiography data sets have been utilized prior, the "noisy" breast enhancement patterns include large blood vessels, tumors, and normal fibroglandular tissue that make this process difficult. Gradient-based algorithms of the current invention, as used for the analysis of typical MR angiography data sets, depict breast enhancement patterns including large blood vessels by obtaining a 3D map, while tumors and normal fibroglandular tissue are excluded from the vasculature map as so desired.

Aspects of the invention utilize methodology as described as follows. Briefly, a 2D maximum intensity projection (MIP) is generated using the subtraction between the contrast-enhanced and the pre-contrast series from the biopsy data set. Note: An MIP map is sometimes referred to as a mipmap which is a computer graphics technique used to achieve an illusion of depth in a two-dimensional representation of a three-dimensional (3D) image. Blood vessels are then identified as the linear components based on wavelet transform and the Hessian matrix. (The Hessian is a square matrix of second-order partial derivatives of a function. It describes the local curvature of a function of many variables.) The breast lesion(s) mapped into the biopsy exam is excluded from this map. The vessels that run out of the initial MIP plane are detected using a rotating 3D rendering display; the connectivity of the vessels between adjacent imaging slices are used to identify these vessels. In one aspect, the vessels found in this 2-step approach are combined to from a 3D vasculature mask.

Once the final biopsy location is chosen by the clinician, a stylet track is sought, thereby connecting the desired biopsy location with the surrounding grid insert entry points, while avoiding vasculature voxels. The shortest track that avoids large vessels is chosen, and the relevant coarse grid insert (and grid insert number) is then displayed to the clinician. In the case in which an entry point is selected that is not the closest path to the lesion, preferential biopsy gun sampling is performed. Instead of the biopsy gun being rotated by 30 degrees between the 12 sampling locations (if the biopsy gun is in the middle of the lesion), more samples are taken below the gun, if the biopsy gun is now positioned superior to the lesion.

Figure 6:
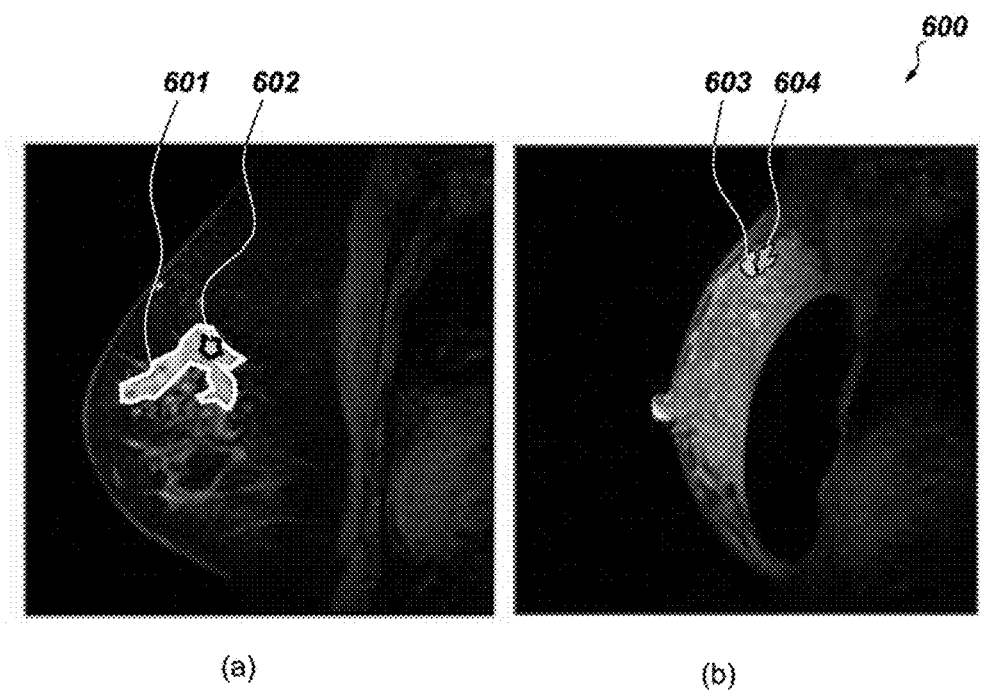
FIG. 6(a) and FIG. 6(b) depict embodiments of the invention in two representative cases of lesions (as outlined), including biopsy location and the intersection of the lesion and biopsy. Note: For easy visualization in clinical practice, characteristic colors are typically utilized in the imaging technique(s) to depict, for example, the lesions in red, the biopsy location in blue, and the intersection of the two in green.

Quality Control to Quantitatively Assess Volume of Tissue Biopsy and Percentage Lesion Fraction of the Extracted Tissue Currently, the assessment of procedure success is done visually, by inspecting the pre-biopsy, contrast enhanced image, and the post-biopsy, last $T_1$-weighted series in the exam. Since the contrast can wash out before the end series, and the signal void can be larger than the biopsied region in the last series (due to susceptibility induced contrast), this assessment can be imperfect and can lead to false negatives. FIG. 6(a) and FIG. 6(b) represent data from two patients, obtained through a preliminary procedure to improve this step. Here, as shown in FIGS. 6(a) and (b), respectively, lesions 601 and 603 are segmented on the first contrast series, and typically highlighted in red (here, outlined). The biopsy region is thresholded out from the last T1-weighted series, typically highlighted in blue (here, illustrated in FIG. 6(b) by outlined attribute 604. The overlay 602 between the lesion and the biopsied region is also depicted, and typically displayed in green, as shown by the outlined lesion tissue 601. Note that while in the first case, FIG. 6(a), an almost perfect biopsy placement was achieved; a less than perfect overlap is evident in the second case, as shown in FIG. 6(b). At the end of the procedure, the clinician is presented the lesion volume, biopsy volume, and a visual and quantitative overlay between the tumor and the biopsy region.

Automated Quality Control

Once the biopsy location is identified by the clinician or the computer, a 3D masking (region growing) algorithm is implemented, enabling 3D lesion segmentation (on the first contrast-enhanced, $T_1$ weighted series). The volume of the lesion is automatically computed. The same process is repeated on the last, biopsy confirmation series, to determine the volume of the biopsied region. This last acquisition (typically a $T_1$ weighted, gradient echo series) is replaced with a spin-echo based acquisition to prevent the artificial increase of the biopsy region volume due to the susceptibility effects of air or biopsy clips. The overlap between the tumor volume and biopsy region volume is then computed. These three (3) volumes, together with the 3D overlay between the tumor region and biopsy region, are displayed immediately after the completion of the last scan to help the clinician assess procedure success.

Figure 8:
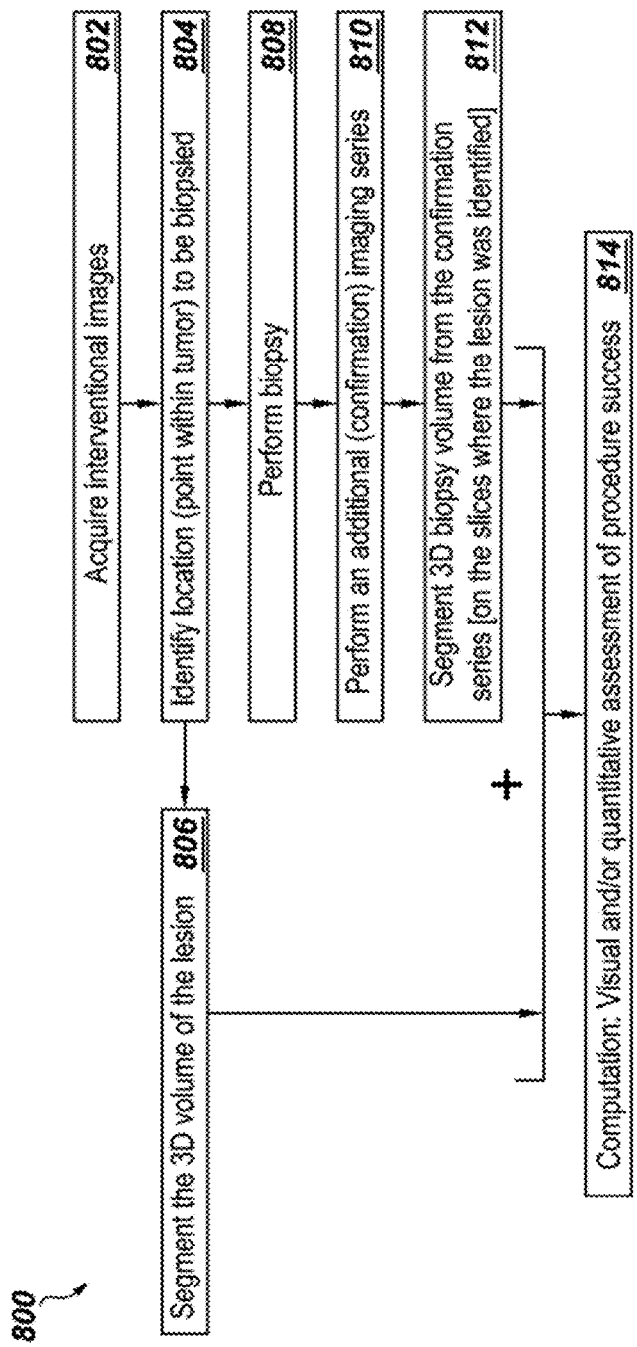
FIG. 8 depicts a schematic workflow of an embodiment of the invention which utilizes quantitative quality control to display to the clinician and overlay between the lesion and the biopsy volume.

FIG. 8 depicts a schematic of one embodiment of the invention to qualitatively and quantitatively assess the biopsy procedure 800. After interventional images are acquired (802), a location is identified within the lesion (or tumor) to be biopsied at 804. The lesion identification can be done manually, by the clinician, using the interventional images. The clinician would click on the point in a computer display that is desired as the center of the biopsy location. In one aspect, a computer algorithm utilizes the interventional images as input. This assumes that contrast is given in the interventional images, and that the lesion enhances in the interventional exam. The algorithm, by way of a computer processor, would designate a single biopsy point, and allocate that point as the center of the tumor. In another aspect, by a computer algorithm, the lesion identification is accomplished using the screening images with the lesion identified and the interventional images, as shown in FIG. 3. The 3D volume of the lesion is then segmented at 806. The segmentation of the lesion and of the biopsy volume can be manual (e.g. by a clinician), semi-automated such that a clinician places a seed and the computer algorithm grows the seed to a 3D volume, or fully automated by the computer processor alone. The above manual and computerized processes may be utilized separately or in combination, as desired.

The biopsy is then performed (808), an additional [confirmation] imaging series acquired (810), and the 3D biopsy volume segmented (812) from the confirmation series on the slices where the lesion had been identified. For clarification, initially, the lesion is segmented. At the end, the void (the region as left behind after biopsy) is segmented. Then, a computation 814 is performed to determine how much of the void included the actual lesion/tumor.

The various embodiments may be implemented in connection with different types of systems including a single modality imaging system and/or the various embodiments may be implemented in or with multi-modality imaging systems. The system is illustrated as an MRI imaging system and may be combined with different types of medical imaging systems, such as a Computed Tomography (CT), Positron Emission Tomography (PET), a Single Photon Emission Computed Tomography (SPECT), as well as an ultrasound system, or any other system capable of generating images, particularly of a human. Moreover, the various embodiments are not limited to medical imaging systems for imaging human subjects, but may include veterinary or non-medical systems for imaging animals and primates.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor. Use of a robot in the magnet and/or to perform the biopsy under MR imaging guidance may also be implemented. In other embodiments, various tissues in other parts of the human or animal body can be imaged.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The invention claimed is:

1. A method for identifying a lesion within a breast during an interventional magnetic resonance imaging (MRI)-guided breast biopsy procedure, the method comprising the steps of:

acquiring one or more screening images of the breast that is uncompressed in a screening exam by an MRI;
segmenting the lesion on the one or more screening images,
creating a three-dimensional (3D) lesion mask of the segmented lesion on the screening images;
acquiring one or more additional images of the breast that is compressed in an interventional MRI-guided breast biopsy procedure to produce interventional images, absent contrast enhancement;
providing a computer processor for performing a non-rigid registration procedure between the uncompressed breast screening images from the screening exam and the compressed breast interventional images from the interventional MRI-guided breast biopsy procedure,
wherein a transformation is produced to relate the one or more uncompressed breast screening images to the one or more compressed breast interventional images;
wherein the step of performing non-rigid registration comprises (a) starting with a translation of the interventional images in order to overlap a field of view of the interventional images with a field of view of the screening images and (b) ending with the non-rigid registration procedure based on mutual information shared between the screening images and the interventional images; and
displaying on a display unit the 3D lesion mask on the interventional images to a clinician to identify a target location of the lesion.

2. The method of claim 1, wherein the step of displaying the 3D lesion mask on the interventional images occurs during the interventional exam.

3. The method of claim 1, wherein the step of acquiring one or more images in the interventional exam further comprises a step of introducing a contrast agent.

4. The method of claim 1, wherein the step of segmenting the lesion, manual seed placement is designated by a clinician.

5. The method of claim 1, further comprising a step of growing a 3D volume around the lesion using thresholds set by the clinician.

6. The method of claim 4, further comprising a step of growing a 3D volume around the lesion using a 3D volume expansion algorithm as controlled by a computer processor.

* * * * *